US012576176B2

(12) United States Patent
Frank et al.

(10) Patent No.: US 12,576,176 B2
(45) Date of Patent: Mar. 17, 2026

(54) QUAT-BASED COMPOSTABLE AND BIODEGRADABLE PREMOISTENED CLEANING AND DISINFECTING WIPES SYSTEM

(71) Applicant: The Clorox Company, Oakland, CA (US)

(72) Inventors: Sophia Frank, Pleasanton, CA (US); John Glauber, Pleasanton, CA (US); Tim Audiss, Pleasanton, CA (US)

(73) Assignee: THE CLOROX COMPANY, Oakland, CA (US)

( * ) Notice: Subject to any disclaimer, the term of this patent is extended or adjusted under 35 U.S.C. 154(b) by 64 days.

(21) Appl. No.: 17/882,227

(22) Filed: Aug. 5, 2022

(65) Prior Publication Data

US 2023/0111060 A1     Apr. 13, 2023

Related U.S. Application Data

(60) Provisional application No. 63/253,387, filed on Oct. 7, 2021.

(51) Int. Cl.
| | |
|---|---|
| *A61L 2/18* | (2006.01) |
| *C11D 1/62* | (2006.01) |

(Continued)

(52) U.S. Cl.
CPC .................. *A61L 2/18* (2013.01); *C11D 1/62* (2013.01); *C11D 3/48* (2013.01); *C11D 17/049* (2013.01); *D21H 11/14* (2013.01); *D10B 2509/00* (2013.01)

(58) Field of Classification Search
CPC ........... C11D 17/049; C11D 3/48; C11D 1/62; A61L 2/18
See application file for complete search history.

(56) References Cited

U.S. PATENT DOCUMENTS

| | | | |
|---|---|---|---|
| 3,929,678 A | 12/1975 | Laughlin et al. |
| 4,171,047 A | 10/1979 | Doyle |

(Continued)

FOREIGN PATENT DOCUMENTS

| | | |
|---|---|---|
| CL | 48074 | 8/2002 |
| CL | 68445 | 7/2020 |

(Continued)

OTHER PUBLICATIONS

Cellulose Biodegradability. Hakkarainen et al. (Year: 2022).*

(Continued)

*Primary Examiner* — Mark Eashoo
*Assistant Examiner* — M. Reza Asdjodi
(74) *Attorney, Agent, or Firm* — Workman Nydegger

(57) ABSTRACT

Pre-dosed wipes and packaged systems of such wipes including a nonwoven substrate formed from renewable natural plant-based fibers or derivatives of such fibers. The pre-dosed wipe as a whole meets applicable biodegradability/compostability standards (e.g., ASTM D6400, EN13432 or the like). The wipe may be a sanitizing or disinfecting wipe, including a quaternary ammonium compound as an antimicrobial agent in the composition with which the substrate is dosed. The composition may also include water and a surfactant. The wipe may be substantially void of thermoplastic fibers, such as PE, PP, PET, as well as so-called biodegradable polyesters and the like (e.g., PHA, PLA, PVOH). The nonwoven substrate may be formed by any of various techniques, an example of which is spunlace. The formulation may have a pH of at least 5 (e.g., 6 to 8), to maintain tensile strength of the natural plant-based substrate.

17 Claims, 5 Drawing Sheets

(51) Int. Cl.

| | | |
|---|---|---|
| *C11D 3/48* | (2006.01) | |
| *C11D 17/04* | (2006.01) | |
| *D21H 11/14* | (2006.01) | |

(56) References Cited

U.S. PATENT DOCUMENTS

| | | | |
|---|---|---|---|
| 4,259,217 A | 3/1981 | Murphy | |
| 4,353,480 A | 10/1982 | McFadyen | |
| 4,565,647 A | 1/1986 | Llenado | |
| 4,624,890 A | 11/1986 | Lloyd et al. | |
| 4,741,944 A | 5/1988 | Jackson et al. | |
| 4,778,048 A | 10/1988 | Kaspar et al. | |
| 5,460,833 A | 10/1995 | Andrews et al. | |
| 5,595,786 A | 1/1997 | McBride et al. | |
| 5,776,872 A | 7/1998 | Giret et al. | |
| 5,883,059 A | 3/1999 | Furman et al. | |
| 5,883,062 A | 3/1999 | Addison et al. | |
| 5,906,973 A | 5/1999 | Ouzounis et al. | |
| 6,221,823 B1 | 4/2001 | Crisanti et al. | |
| 6,346,279 B1 | 2/2002 | Rochon | |
| 6,429,183 B1 | 8/2002 | Leonard et al. | |
| 6,525,071 B2 * | 2/2003 | Dyer | A61P 31/02 |
| | | | 514/320 |
| 6,551,980 B1 | 4/2003 | Wisniewski et al. | |
| 6,699,825 B2 * | 3/2004 | Rees | C11D 17/049 |
| | | | 510/432 |
| 6,803,057 B2 | 10/2004 | Ramirez et al. | |
| 6,812,196 B2 | 11/2004 | Rees et al. | |
| 6,825,158 B2 * | 11/2004 | Mitra | C11D 1/62 |
| | | | 510/432 |
| 6,936,597 B2 | 8/2005 | Greenwald et al. | |
| 7,008,600 B2 | 3/2006 | Katsigras et al. | |
| 7,070,737 B2 | 7/2006 | Bains et al. | |
| 7,598,214 B2 | 10/2009 | Cusack et al. | |
| 7,605,096 B2 | 10/2009 | Tomarchio et al. | |
| 7,632,797 B2 | 12/2009 | Moses et al. | |
| 7,658,953 B2 | 2/2010 | Bobbert | |
| 7,696,109 B2 | 4/2010 | Ouellette et al. | |
| 7,696,143 B2 | 4/2010 | McCue et al. | |
| 7,915,207 B2 | 3/2011 | Herdt et al. | |
| 8,093,199 B2 | 1/2012 | Johnson et al. | |
| 8,268,334 B2 | 9/2012 | Dreilinger et al. | |
| 8,541,356 B2 | 9/2013 | Saint Victor | |
| 8,569,220 B2 | 10/2013 | Gaudreault | |
| 8,575,084 B2 | 11/2013 | Gaudreault | |
| 8,648,027 B2 | 2/2014 | Mitchell et al. | |
| 8,772,185 B2 | 7/2014 | Jelonek et al. | |
| 9,006,165 B2 | 4/2015 | Mitchell et al. | |
| 9,096,821 B1 * | 8/2015 | Hope | C11D 3/2017 |
| 9,234,165 B2 | 1/2016 | Hope et al. | |
| 9,555,167 B2 * | 1/2017 | Schmid | A61B 46/00 |
| 9,988,594 B2 | 6/2018 | Hope et al. | |
| 10,064,409 B2 | 9/2018 | Hazenkamp et al. | |
| 10,076,115 B2 | 9/2018 | Salminen et al. | |
| 10,358,624 B1 | 7/2019 | Mitchell et al. | |
| 10,421,929 B2 | 9/2019 | Coulter et al. | |
| 10,975,341 B2 | 4/2021 | Dani | |
| 2002/0165260 A1 * | 11/2002 | Dyer | A61P 31/02 |
| | | | 514/642 |
| 2003/0119705 A1 | 6/2003 | Barnabas et al. | |
| 2004/0157524 A1 | 8/2004 | Polat et al. | |
| 2005/0215458 A1 * | 9/2005 | Lalum | C11D 3/2003 |
| | | | 510/438 |
| 2007/0190172 A1 | 8/2007 | Bobbert | |
| 2007/0295465 A1 | 12/2007 | Dyer et al. | |
| 2008/0003906 A1 | 1/2008 | Hill et al. | |

| | | | |
|---|---|---|---|
| 2008/0142023 A1 * | 6/2008 | Schmid | A61L 31/16 |
| | | | 128/849 |
| 2012/0034278 A1 * | 2/2012 | Schwarz | A61K 31/405 |
| | | | 514/420 |
| 2012/0039974 A1 * | 2/2012 | Napolitano | C11D 3/2041 |
| | | | 427/430.1 |
| 2013/0028990 A1 | 1/2013 | Smith et al. | |
| 2014/0171512 A1 * | 6/2014 | Kloeppel | A01N 47/44 |
| | | | 514/635 |
| 2015/0125502 A1 * | 5/2015 | Colurciello | A61L 2/18 |
| | | | 424/409 |
| 2015/0272836 A1 * | 10/2015 | Bonner | A61K 8/06 |
| | | | 15/104.93 |
| 2019/0085274 A1 * | 3/2019 | Dani | C11D 1/62 |
| 2019/0282458 A1 * | 9/2019 | Villarreal, Jr. | A61K 8/42 |
| 2020/0198288 A1 | 6/2020 | Dani et al. | |
| 2020/0198303 A1 | 6/2020 | Dani et al. | |
| 2020/0305437 A1 * | 10/2020 | McGeechan | A61P 31/10 |
| 2020/0368558 A1 * | 11/2020 | Chiou | A61K 8/0208 |
| 2021/0029999 A1 * | 2/2021 | Hayward | C11D 1/94 |
| 2021/0038484 A1 * | 2/2021 | Chiou | A61K 8/0208 |
| 2022/0025562 A1 | 1/2022 | White et al. | |
| 2022/0096345 A1 * | 3/2022 | Chiou | A61K 8/064 |
| 2022/0364307 A1 | 11/2022 | Latten | |
| 2022/0370302 A1 | 11/2022 | Marsh et al. | |
| 2023/0111060 A1 * | 4/2023 | Frank | C11D 3/48 |
| | | | 510/295 |
| 2023/0151521 A1 | 5/2023 | Porcher et al. | |
| 2023/0413812 A1 * | 12/2023 | Joshi | A01N 31/02 |
| 2024/0424159 A1 | 12/2024 | Olson et al. | |

FOREIGN PATENT DOCUMENTS

| | | |
|---|---|---|
| CL | 2021001612 A1 | 12/2021 |
| CL | 2021001606 A1 | 2/2022 |
| CL | 2021002497 A1 | 7/2022 |
| CN | 116856112 | 10/2023 |
| EP | 0992338 A2 | 4/2000 |
| EP | 1303661 A1 | 4/2003 |
| EP | 1687136 A2 | 8/2006 |
| EP | 1861529 A1 | 12/2007 |
| EP | 2843034 A1 | 3/2015 |
| JP | 2024-035481 | 3/2024 |
| WO | 99/18180 A1 | 4/1999 |
| WO | 99/53006 A1 | 10/1999 |
| WO | 01/32826 | 5/2001 |
| WO | 01/49912 A1 | 7/2001 |
| WO | 2004/067194 A2 | 8/2004 |
| WO | 2004/104147 A1 | 12/2004 |
| WO | 2017/174959 A1 | 10/2017 |
| WO | 2018/184047 A1 | 10/2018 |
| WO | 2021/148498 A1 | 7/2021 |

OTHER PUBLICATIONS

Final Office Action received for U.S. Appl. No. 17/374,420, mailed on Jul. 18, 2024, 8 pages.

Non-Final Office Action received for U.S. Appl. No. 17/374,420, mailed on Mar. 28, 2024, 7 pages.

Non-Final Office Action received for U.S. Appl. No. 17/374,420, mailed on Nov. 21, 2024, 9 pages.

Final Office Action received for U.S. Appl. No. 17/374,420, mailed on Jun. 12, 2025, 10 pages.

Tezel et al., "Quaternary ammonium disinfectants: microbial adaptation, degradation and ecology", Current Opinion in Biotechnology, vol. 33, Apr. 10, 2015, pp. 296-304.

\* cited by examiner

QUAT-BASED COMPOSTABLE AND BIODEGRADABLE PREMOISTENED CLEANING AND DISINFECTING WIPES SYSTEM

CROSS REFERENCE TO RELATED APPLICATIONS

The present application claims the benefit of U.S. Provisional Patent Application Ser. No. 63/253,387, filed on Oct. 7, 2021, the disclosure of which is incorporated by reference in its entirety

BACKGROUND OF THE INVENTION

1. The Field of the Invention

The present invention relates to cleaning wipes, e.g., pre-loaded cleaning wipes that are formed from single or multi-layer substrates, and which are pre-loaded during manufacture with a cleaning composition. Such pre-loaded wipes may be provided within a container (e.g., packaged therein during manufacture).

2. Description of Related Art

Numerous cleaning wipes are available, e.g., such as CLOROX DISINFECTING WIPES. While such wipes provide good overall cleaning and disinfection characteristics, versatility, and convenience, there is a continuing need for improved cleaning wipes.

For example, a significant portion of the nonwoven substrate used in manufacturing such existing wipes is formed from materials sourced from non-renewable, petrochemical sources, where such materials (e.g., typically polypropylene and/or PET) are not renewably sourced, biodegradable or compostable. As such wipes are typically used a single time and then disposed of, there is a significant environmental impact associated with such disinfecting or sanitizing wipes.

While there has been some interest in developing more compostable disinfecting or sanitizing wipes using regenerated cellulose substrates dose with citric acid or lactic acid based formulations, such wipes necessarily have low pH, which can weaken the substrate, they are typically not safe for use on surfaces incompatible with acids (e.g., marble and some ceramics), and they exhibit poor performance in cleaning greasy or oily soils. It would be an advantage to provide a disinfecting or sanitizing wipe that was formed from renewable plant-based materials, and was biodegradable and/or compostable. It would be a further advantage if such a wipe were also capable of providing antimicrobial efficacy similar to existing wipes, if such a wipe had similar performance in cleaning up oily or greasy soils, and if such a wipe provided safety across a wide variety of surfaces (e.g., ceramic, marble, etc.).

BRIEF SUMMARY

As a first matter, biodegradability or compostability of a given article is not ensured even if all the components included in such article are individually biodegradable or compostable under the same conditions (e.g., under ASTM D6400, ASTM D5338, or ASTM D5271). In other words, even if a wipe substrate and the disinfecting composition itself, or the components thereof were compostable or biodegradable on their own, this does not mean that a disinfecting or sanitizing wipe formed from such components would necessarily also be biodegradable and/or compostable. Such is the case because biodegradability (and compostability) are complex biological processes, with the ability to meet any given standard (e.g., ASTM D6400, ASTM D5338 or ASTM D5271) dependent on composition components, concentrations, thickness and other geometric and physical or mechanical characteristics of the substrate, and interactions between wipe components, etc. The ability to achieve biodegradability or compostability for any given component affects, and is affected by, the other components in the article. At the end of the day, what is important, is the ability to achieve a desired biodegradability or compostability standard for the article as a whole. In addition to the impossibility of predicting whether a given combination (substrate and loaded disinfecting, sanitizing or other cleaning composition) will meet any given ASTM or other standard for assessing biodegradability or compostability, it is also necessary that any designed disinfecting wipe also be able to achieve desired standards of antimicrobial efficacy. For example, selections perhaps required to achieve biodegradability or compostability may interfere with the ability to achieve needed antimicrobial efficacy. For example, because biodegradability and compostability depend on the action of microbes within the tested disposal or composting environment, it is somewhat counterintuitive and surprising that it would be possible to provide a wipe loaded with an antimicrobial composition, where such wipe would be biodegraded or composted, rather than the antimicrobial composition inhibiting the achievement of such microbial biodegradation or composting.

In one aspect, the present invention provides disinfecting or sanitizing wipes that are preloaded with a sanitizing or disinfecting composition, where the article as a whole meets compostability or biodegradability standards (e.g., ASTM D6400 or EN13432), while at the same time providing a desired level of antimicrobial efficacy (e.g., sanitization or disinfection, e.g., in the form of a given log reduction in the population of a given target microbe). In an embodiment, the disinfecting or sanitizing wipe includes a nonwoven substrate comprising plant-based fibers derived from a renewable natural plant-based material (e.g., such as cellulose). The wipe is pre-loaded with a sanitizing or disinfecting composition that comprises a quaternary ammonium compound as an antimicrobial agent, a surfactant, and water, where the composition has a pH of at least 5 (e.g., about 6 to 8), wherein the composition provides sanitization or disinfection against a target microbe within a given time period (e.g., within 10 minutes or less), and where the sanitizing or disinfecting wipe is compostable (e.g., under ASTM D6400 or EN13432, or the like) and each component of the composition is present at less than 1% dry weight of the wipe as a whole or components that exceed 1% dry weight of the wipe as a whole all pass a biodegradation test (e.g., ASTM D5338 or similar) where 90% or more of such component biodegrades within 180 days when tested alone. In an embodiment, the composition does not include a carboxylic acid disinfecting agent (e.g., citric acid, lactic acid or the like, as an antimicrobial agent), biguanides, peroxides, or hypohalite disinfecting agents. The wipe may be free or substantially free of thermoplastic fibers typically used in wipe manufacture, including but not limited to polypropylene, PET, polyethylene, or even polyesters or similar "green" thermoplastic resins that may exhibit improved compostability or biodegradability (e.g., PHA, PLA, PVOH, etc.)

Another example of a sanitizing or disinfecting wipe may include a nonwoven substrate comprising fibers that are a cellulose derivative, and a sanitizing or disinfecting composition loaded onto the nonwoven substrate at a loading ratio of from 2:1 to 6:1 by weight. The sanitizing or disinfecting composition includes a quaternary ammonium compound as an antimicrobial agent, a surfactant, and water, where at least 90% by weight of the composition is water. The composition has a pH of from 6 to 8, provides sanitization or disinfection against a target microbe within 10 minutes, or 5 minutes or less, wherein the sanitizing or disinfecting wipe as a whole (i.e., the loaded wipe) is compostable under ASTM D6400, EN13432, or similar biodegradability or composability standard (e.g., ASTM D5338 or ASTM D5271). Each component of the composition is present at less than 1% dry weight of the wipe as a whole or components that exceed 1% dry weight of the wipe as a whole all pass a biodegradation test (e.g., ASTM D5338, or the like) where 90% or more of such component biodegrades within 180 days when tested alone.

In any such embodiments, the nonwoven substrate may comprise a cellulose derivative, and/or be derived from pulp fibers. Non-limiting examples of such a nonwoven substrate include viscose or lyocell. The nonwoven substrate is a fibrous nonwoven, and may be formed by any suitable technique as will be apparent to those of skill in the art.

In an embodiment, the nonwoven substrate may be void of "green" polyesters, for example polyesters such as PLA, PHA or similar "green" fibers such as PVOH, which may exhibit some level of biodegradability or compostability. The nonwoven substrate may be void of traditional petrochemically derived thermoplastic fibers (e.g., PET, PP, PE and the like), which are notoriously well known to exhibit no substantial biodegradability or compostability within any reasonable time frame (e.g., 5 years or less). Generally speaking, in an embodiment, the nonwoven substrate may be void of thermoplastic fibers, as pulp, cellulose, and cellulose derived fibers (e.g., such as viscose and lyocell) are not thermoplastic.

In an embodiment, the quaternary ammonium compound is present as two or more quaternary ammonium compounds, the quaternary ammonium compounds collectively being present in an amount of greater than 1% by dry weight of the wipe as a whole, but where each of the quaternary ammonium compounds are individually present in an amount of less than 1% by dry weight of the wipe as a whole.

In an embodiment, the sanitizing or disinfecting composition may comprise at least 90%, or at least 95% water by weight.

In an embodiment, the sanitizing or disinfecting composition is loaded onto the nonwoven substrate at a loading ratio of from 2:1 to 10:1, 2:1 to 8:1, 2:1 to 6:1, or from 2.5:1 to 4.5:1. The particular loading ratio selected is important, as loading ratio can affect not just the antimicrobial efficacy, but also the ability to meet the compostability standard for the wipe as a whole, under ASTM D6400 or other applicable biodegradability or compostability standard.

In an embodiment, the sanitizing or disinfecting composition has a moderate pH, near a neutral pH of 7, rather than being strongly acidic. For example, Applicant has found that significantly more acidic pH values (e.g., less than 5, such as 2-3) can have a detrimental effect on the strength of the particular selected non-woven substrate over time, as acidic sanitizing or disinfecting compositions tend to weaken the fibers of the substrate over time, resulting in a wipe that is too weak for use (e.g., having tensile strength, particularly CD tensile strength of less than 3 $lb_f$) within several weeks after loading. Such a shelf life (only several weeks or a few months) is undesirable.

In addition, low pH values (e.g., of 3 or less) limit the ability to safely use such a wipe on marble and some ceramic surfaces, which are attacked by the acid present in such compositions. Finally, Applicant has noted that compositions exhibiting low pH, based on use of citric acid, lactic acid, or other organic acid(s) for sanitization or disinfection exhibit poor performance in such a wipe's ability to effectively clean away oily or greasy soils. As such, sanitizing and disinfecting compositions (or even cleaning compositions more generally) including relatively high concentrations (e.g., at least 0.1%, 0.3%, 0.5%, or 1% by weight) of organic acids are thus not suitable for use, as contemplated herein.

In an embodiment, the surfactant can be present in an amount of greater than 1% by dry weight of the wipe as a whole, and when tested alone, at least 90% of the surfactant biodegrades (e.g., under ASTM D5338 or other appropriate standard) within an appropriate time frame (e.g., such as 180 days).

In an embodiment, wipe is such that the composition provides at least a 3-log reduction against a target microbe within 4 minutes or less. In another embodiment, wipe is such that the composition provides at least a 3-log reduction against a target microbe within 1 minute or less.

While the present wipes are largely described in the context of disinfecting or sanitizing wipes, where the composition loaded onto the wipe includes an antimicrobial agent (e.g., a quaternary ammonium compound), it will be appreciated that other biodegradable and/or compostable wipes could be provided more generally, as cleaning wipes, to provide general cleaning, without necessarily providing any significant antimicrobial efficacy. Such embodiments may not necessarily include the quaternary ammonium compound antimicrobial agent, but may include water, a surfactant, and any other adjuvants as desired, so long as the wipe as a whole is configured to meet applicable biodegradability or compostability standards under ASTM D6400, EN13432, ASTM D5338, ASTM D5271 or the like.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings.

DETAILED DESCRIPTION OF THE PREFERRED EMBODIMENTS

I. Definitions

Figure 1A:
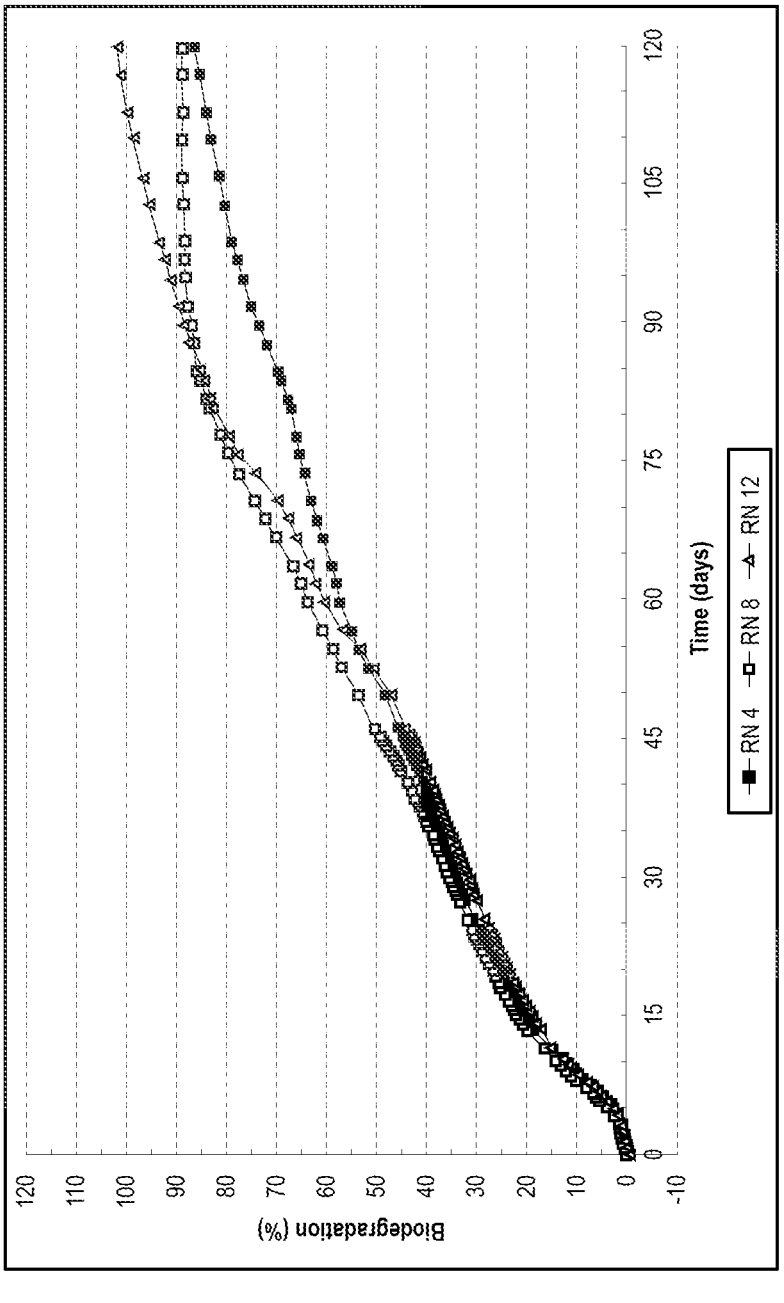
FIG. 1A charts the biodegradation over time, using ASTM D5338, for 3 runs of Dehypon LS54, which is a nonionic surfactant that is a fatty alcohol alkoxylate formed from $C_{12}$-$C_{14}$ fatty alcohols and ethylene oxide and/or propylene oxide.

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more surfactants.

Unless otherwise stated, all percentages, ratios, parts, and amounts used and described herein are by weight.

Numbers, percentages, ratios, or other values stated herein may include that value, and also other values that are about or approximately the stated value, as would be appreciated by one of ordinary skill in the art. As such, all values herein are understood to be modified by the term "about". Such values thus include an amount or state close to the stated amount or state that still performs a desired function or achieves a desired result. A stated value should therefore be interpreted broadly enough to encompass values that are at least close enough to the stated value to perform a desired function or achieve a desired result, and/or values that round to the stated value. The stated values include at least the variation to be expected in a typical manufacturing or other process, and may include values that are within 10%, within 5%, within 1%, etc. of a stated value.

Some ranges may be disclosed herein. Additional ranges may be defined between any values disclosed herein as being exemplary of a particular parameter. All such ranges are contemplated and within the scope of the present disclosure.

As used herein, the term "between" is inclusive of any endpoints noted relative to a described range.

In the application, effective amounts are generally those amounts listed as the ranges or levels of ingredients in the descriptions, which follow hereto. Unless otherwise stated, amounts listed in percentage ("%'s") are in weight percent (based on 100% active) of any composition.

The phrase 'free of' or similar phrases if used herein means that the composition or article comprises 0% of the stated component, that is, the component has not been intentionally added. However, it will be appreciated that such components may incidentally form thereafter, under some circumstances, or such component may be incidentally present, e.g., as an incidental contaminant.

The phrase 'substantially free of' or similar phrases as used herein means that the composition or article preferably comprises 0% of the stated component, although it will be appreciated that very small concentrations may possibly be present, e.g., through incidental formation, contamination, or even by intentional addition. Such components may be present, if at all, in amounts of less than 1%, less than 0.5%, less than 0.25%, less than 0.1%, less than 0.05%, less than 0.01%, less than 0.005%, less than 0.001%, or less than 0.0001%. In some embodiments, the compositions or articles described herein may be free or substantially free from any specific components not mentioned within this specification.

As used herein, "disposable" is used in its ordinary sense to mean an article that is disposed or discarded after a limited number of usage events, preferably less than 25, more preferably less than about 10, and most preferably after a single usage event. The wipes disclosed herein are typically disposable.

As used herein, the term "substrate" is intended to include any material that is used to clean an article or a surface. Examples of cleaning substrates include, but are not limited to, wipes, mitts, pads, or a single sheet of material which is used to clean a surface by hand or a sheet of material which can be attached to a cleaning implement, such as a floor mop, handle, or a hand held cleaning tool, such as a toilet cleaning device. The term "substrate" is also intended to include any material that is used for personal cleansing applications. These substrates can be used for hard surface, soft surface, and personal care applications. Such substrates may typically be in the form of a wipe.

Such substrates may be formed of a structure of individual fibers which are interlaid, typically in a manner that is not identifiable (e.g., a nonwoven). The nonwoven substrates, or layers used to make up such a nonwoven substrate included in the present substrates may be formed by any suitable process. For example, they may be meltblown, spunbond, spunlaid, SMS (spunbond-meltblown-spunbond), coformed, carded webs, thermal bonded, thermoformed, spunlace, hydroentangled, hydroembossed, needled, or chemically bonded. Various processes for forming such nonwovens will be apparent to those of skill in the art, many of which are described in U.S. Pat. No. 7,696,109, incorporated herein by reference in its entirety. EP Applications EP992338, EP1687136, EP1861529, EP1303661, and US2004/0157524 are also herein incorporated by reference, each in its entirety. These references describe various nonwoven structures which are generally illustrative, and which may be modified by using the contemplated plant-based renewable biodegradable and/or compostable fibers described herein rather than the synthetics typically employed in the prior art. Where the employed fibers are not thermoplastic (e.g., various pulp or cellulose derivatives), the processes used to form the nonwoven may of course not rely on melt-softening or thermoplasticity. Spunlace and hydroentangling are non-limiting examples of such processes.

The terms "wipe", "substrate" and the like may thus overlap in meaning, and while "wipe" may typically be used herein for convenience, it will be appreciated that this term may often be interchangeable with "substrate".

As used herein, "wiping" refers to any shearing action that the wipe undergoes while in contact with a target surface. This includes hand or body motion, substrate-implement motion over a surface, or any perturbation of the substrate via energy sources such as ultrasound, mechanical vibration, electromagnetism, and so forth.

The cleaning compositions dosed onto the substrate as described herein may provide sanitization, disinfection, or sterilization, other cleaning, or other treatment. As used herein, the term "sanitize" shall mean the reduction of "target" contaminants in the inanimate environment to levels considered safe according to public health ordinance, or that reduces a "target" bacterial population by significant numbers where public health requirements have not been established. By way of example, an at least 99% reduction in bacterial population within a 24 hour time period is deemed "significant." Greater levels of reduction (e.g., 99.9%, 99.99%, etc.) are possible, as are faster treatment times (e.g., within 10 minutes, within 5 minutes, within 4 minutes, within 3 minutes, within 2 minutes, within 1 minute, or within 30 seconds), when sanitizing or disinfecting.

As used herein, the term "disinfect" shall mean the elimination of many or all "target" pathogenic microorganisms on surfaces with the exception of bacterial endospores.

As used herein, the term "sterilize" shall mean the complete elimination or destruction of all forms of "target" microbial life and which is authorized under the applicable regulatory laws to make legal claims as a "sterilant" or to have sterilizing properties or qualities.

Some embodiments may provide for at least a 2 or more log reduction (e.g., 3-log reduction, 4-log reduction, 5-log reduction, or 6-log reduction) in a bacterial population within a designated time period (e.g., 10 minutes, 5 minutes, 4 minutes, 3 minutes, 2 minutes, 1 minute, 30 seconds, or the like). A 2-log reduction is equivalent to a 99% reduction, a 3-log reduction is equivalent to at least a 99.9% reduction, a 4-log reduction is equivalent to at least a 99.99% reduction, a 5-log reduction is equivalent to at least a 99.999% reduction, etc. An example of a target microbe may be *Staphylococcus aureus*. It will be appreciated that antimicrobial efficacy can also be achieved against other target microbes, numerous examples of which will be apparent to those of skill in the art. It will also be appreciated that the present cleaning compositions need not include an antimicrobial agent (e.g., a quaternary ammonium compound or the like), where sanitization or disinfection is not necessarily desired.

In reference to various standardized tests (e.g., ASTM 6400 or other tests), it will be understood that reference to any such standard refers to the latest update (if any) of such standard, unless otherwise indicated. Any such referenced standards are incorporated herein by reference, in their entirety.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

II. Exemplary Nonwoven Substrates

In an aspect, the present invention is directed to preloaded nonwoven substrates, where they are specifically formed from materials that are more environmentally friendly as compared to the non-renewable, non-biodegradable, non-compostable materials typically employed as synthetic fibers in such wipes. In addition, the entire combination, i.e., the loaded wipe as a whole, meets applicable compostability requirements (e.g., ASTM D6400, EN13432, ASTM D5338, ASTM D5271 or the like). The fibers and/or nonwoven may be formed by any suitable technique, e.g., including but not limited to meltblown, spunbond, spunlaid, SMS (spunbond-meltblown-spunbond), coform, carded webs, thermal bonded, thermoformed, spunlace, hydroentangled, hydroembossed, needled, or chemically bonded, and any combinations thereof. In an embodiment, the nonwoven may be spunlace, or another process that does not rely on melt-softening or thermoplasticity, where the employed fibers are cellulose or other pulp materials or derivatives thereof, such as viscose, rayon or lyocell.

In one embodiment, the nonwoven substrate may be comprised of multiple layers (e.g., 2 or 3 layers). In another embodiment, the substrate may be formed from a single layer. Where different layers are present, the initially separate layers may be bonded to one another through any of various suitable techniques that will be apparent to those of skill in the art. For example, hydroentangling, needling or any other technique may be used to bond such layers to one another.

No matter the process by which the dry nonwoven substrate is formed, once formed, a desired cleaning composition may be loaded onto the nonwoven substrate.

Various pulp or cellulose materials, or their derivatives may be particularly suitable for use in the present nonwoven substrates, because they are renewably sourced, and readily biodegradable and/or compostable. While in an embodiment, it may be possible to incorporate some fraction of biodegradable or compostable polyesters, polyvinyl alcohols, or polyvinyl acetates as binder fibers (e.g., (e.g. PHA, PVOH, PVA, and/or PLA) in forming the present nonwoven substrates, as described in Applicant's U.S. patent application Ser. No. 17/374,420, filed Jul. 13, 2021, which is herein incorporated by reference in its entirety, in another embodiment, no such thermoplastic binder fibers are included in the nonwoven substrate. In an embodiment, the substrate fibers may consist, or consist essentially of viscose, lyocell, or a similar pulp or cellulose derivative material. In an embodiment, various synthetic thermoplastic materials typically included in a nonwoven substrate, but which interfere with the ability to achieve biodegradability and/or compostability, are not included in the substrate. Examples of such materials include, but are not limited to polyethylene, polypropylene, PET, PVC, polyacrylics, polyamides, polystyrenes, and the like.

The fibers of the nonwoven substrate may be formed of natural fibers or derivatives of natural fibers (e.g., regenerated cellulose), and may comprise any of various natural fibers, or derivatives thereof. In an embodiment, such natural fibers may comprise pulp fibers (e.g., wood pulp), or be derived from such fibers. Non-limiting examples of such renewable plant-based naturally derived fibers include, but are not limited to cellulose fibers, regenerated cellulose fibers (e.g., viscose, lyocell, modal, and/or rayon), cotton and the like. Such natural fibers may typically be of shorter length than typical synthetic fibers. By way of example, those of skill in the art will appreciate that viscose can be formed through treatment of pulp or cellulose fibers with sodium hydroxide and carbon disulfide, and that lyocell fibers can be formed through treatment of cellulose or pulp fibers in amine oxide, which is then spun into fibers. Such renewable fibers, and nonwovens formed therefrom are available from various suppliers.

The basis weight of the nonwoven substrates or individual layers thereof may be expressed in grams per square meter (gsm), and may be, for example, no more than 200 gsm, no more than 150 gsm, no more than 100 gsm, such as from 5 to 80 gsm, or from 10 to 60 gsm.

It will be appreciated that the present wipes may include any of various textures, or perhaps no texture at all. Various textures are shown in FIGS. 1A-1D and FIGS. 7A-7F of Applicant's U.S. application Ser. No. 16/710,676 filed on Dec. 11, 2019, herein incorporated by reference in its entirety.

While it may be possible to integrate biodegradable and/or compostable polyester fibers, polyvinyl alcohol fibers, and/or polyvinyl acetate fibers into the nonwoven substrate, in a particular embodiment, 100% of the fibers in the nonwoven substrate are plant-based natural or naturally derived fibers (e.g., viscose or lyocell). In another embodiment, at least 50%, at least 60%, at least 70%, at least 80%, at least 90%, or at least 95%, by weight of the fibers are such renewable plant-based natural or naturally derived fibers.

While a wide variety of synthetic materials are sometimes used as binder fibers, e.g., most typically polypropylene and/or PET, these materials are not biodegradable or compostable, as defined by ASTM D6400, or EN13432. Advantageously, the nonwoven substrate may consist essentially of plant-based biodegradable and/or compostable fibers, aiding the wipe as a whole to meet such biodegradability/compostability standards. In an example, the wipe may be free of, or substantially free of fibers that do not meet such standards, i.e., free of polyethylene, polypropylene, PET, PVC, polyacrylics, polyamides, polystyrenes, or the like.

Individual layers, or the nonwoven substrate as a whole may have a basis weight of no more than 200 gsm, no more than 150 gsm, no more than 100 gsm, such as from 5 to 80 gsm, or from 10 to 60 gsm.

It may be advantageous that any processing that the nonwoven substrate undergoes (e.g., calendaring, drying, or the like), be at a temperature that is sufficiently low to ensure that any pulp or other plant-based natural or naturally derived fibers do not ignite, or become embrittled or discolored due to "burning", which may occur near the paper ignition temperature of 233° C.

The nonwoven substrates may be packaged within any desired container system. Examples of such include, but are not limited to flex packs, cylinders, tubs, or other containers for storage and dispensing. The wipes may typically be pulled through an orifice such as typically provided with such containers, without fear of shredding or delamination of any included layers, even where all or nearly all of the fibers of the nonwoven substrate comprise pulp or other fibers derived from a plant-based natural source (e.g., viscose or lyocell fibers).

In some embodiments, it may be desirable to provide the substrate with a lofted structure, so as to increase the bulk and thickness of the substrate, where such lofted characteristics may not otherwise be provided, particularly by synthetic fibers. Such lofting may be provided by any suitable technique that may increase the bulk and thickness of the layer, by adding lofted material thereto, which includes gaps, air pockets, and/or a fuzzy, lofted characteristic.

III. Cleaning Composition

A. Antimicrobial Agent

Many cleaning composition components as known within the art may be suitable for use in the present pre-dosed wipes. In an embodiment, the cleaning composition is an aqueous composition, including at least 70%, at least 80%, at least 90%, or at least 95% water by weight (e.g., 95% to 99% water). The composition may include a quaternary ammonium compound as an antimicrobial agent. For example, the quaternary ammonium compound may be included from 0.05%, from 0.1%, up to 5%, up to 4%, up to 3%, up to 2%, up to 1.5%, or up to 1% by weight of the cleaning composition. In an embodiment, the quaternary ammonium compound is present as two or more quaternary ammonium compounds. When at least two quaternary ammonium compounds are present, the first quaternary ammonium compound is present in an amount of less than 1% by dry weight of the loaded wipe as a whole and the second quaternary ammonium compound is present in an amount of less than 1% by dry weight of the loaded wipe as a whole. Collectively the two or more quaternary ammonium compounds may be present in an amount of greater than 1% to about 5%, by dry weight of the loaded wipe as a whole. For example, the composition of Table 2A in the Examples section includes 0.73% collectively, of a first quaternary ammonium compound and a second quaternary ammonium compound (i.e., 0.73%, including water weight, of the composition itself). The loaded wipe, on a dry basis (i.e., excluding water, but including the substrate weight) includes 1.43% dry weight collectively of the two quaternary ammonium compounds. Each quaternary ammonium compound alone is present at less than 1% dry weight.

Quaternary ammonium compounds have broad spectrum antimicrobial properties. A variety of different quaternary ammonium compounds can be used in the cleaning composition. Non-limiting examples of quaternary ammonium compounds are typically halides (e.g., a chloride) of alkyldimethylbenzylammonium, alkyldimethylethylbenzylammonium, alkyldimethylammonium, or the like. The alkyl groups of such quaternary ammonium compounds may typically range from $C_{12}$ to $C_{18}$. Quaternary ammonium compounds are described in more detail in U.S. Pat. No. 6,825,158, incorporated by reference herein, and will already be familiar to those of skill in the art. In particular, the included quaternary ammonium compound(s) are able to meet applicable biodegradability and/or compostability requirements. For example, even though such quaternary ammonium compounds are synthetic, certain quaternary ammonium compounds are biodegradable and/or compostable. The selected quaternary ammonium compound(s) may be "readily biodegradable", meaning that the material exhibits ≥60% biodegradation under OECD 301A-F/ASTM D7373 within 28 days.

In an embodiment, the quaternary ammonium compound is the only included antimicrobial agent. For example, no organic acids may be present in sufficiently high amounts to serve as an antimicrobial agent. While such organic acids can provide antimicrobial efficacy at relatively high concentrations, and low pH, the low pH has been found by applicant to interfere with the ability to maintain tensile strength in the nonwoven substrate, and also limits surface compatibility, and interferes with the ability to effectively clean oily or greasy soils. For example, it is advantageous that the nonwoven substrate provide a tensile strength (particularly in the cross direction) of at least 3 $lb_f$ to ensure that the wipe does not tear when pulling wipes from a given dispenser, and that the wipe does not tear during typical use.

The low pH associated with use of organic acid-based disinfecting or sanitizing compositions has been found by Applicant to degrade the viscose, lyocell or similar plant-based renewable natural fiber materials contemplated for use in the substrate, causing them to not be able to maintain at least 3 $lb_f$ of tensile strength over the desired shelf-life of the present wipes (e.g., at least 6 months, at least 12 months, at least 18 months, at least 24 months or the like, stored at about 70° F. (21° C.) ambient temperature). In other words, the organic acid attacks the substrate, causing the substrate to be too weak after a few weeks or months of such storage. Examples of such organic acids that are sometimes used as antimicrobial agents, include but are not limited to, citric acid, lactic acid, glycolic acid, and other carboxylic acids. While such acids may not be used as antimicrobial agents in the present embodiments, one or more of such acids may be present in a small amount, for another purpose, such as a buffer or pH adjuster (e.g., in an amount of less than 0.1%, less than 0.05%, or no more than 0.01% by weight of the composition).

B. Solvents

The composition may include a solvent, such as a glycol ether solvent. Exemplary glycol ether solvents include, but are not limited to, ethylene glycol monopropyl ether, ethylene glycol monobutyl ether, ethylene glycol monohexyl ether, ethylene glycol phenyl ether, propylene glycol n-propyl ether, propylene glycol monobutyl ether, propylene glycol t-butyl ether, diethylene glycol monoethyl or monopropyl or monobutyl ether, di- or tri-polypropylene glycol methyl or ethyl or propyl or butyl ether, acetate and/or propionate esters of glycol ethers. The glycol ether or other solvent may be included from 0.1%, from 0.25%, up to 5%, up to 4%, up to 3%, up to 2%, or up to 1% by weight of the cleaning composition. Other solvents, surfactants, and various other adjuvants often included in cleaning compositions may optionally be present. While some embodiments may include lower alcohol solvents (e.g., $C_1$-$C_4$ alcohols), the amount of such volatile solvents may be limited, e.g., to less than 10%, less than 5%, less than 3%, less than 2%, less than 1%, less than 0.5%, or less than 0.3% by weight. Other alcohol solvents can also be used (e.g., $C_5$ and higher, such as $C_6$ to $C_{16}$, $C_8$ to $C_{12}$, $C_{10}$, etc.). In some embodiments, the composition may be free of, or substantially free of, such lower alcohol or other highly volatile solvents.

C. Surfactants

Those of skill in the art will appreciate that any among a wide variety of surfactants (e.g., anionic, cationic, non-ionic, zwitterionic, and/or amphoteric) may be included in the cleaning composition, as desired, so long as the resulting loaded wipe can meet applicable biodegradability and/or compostability standards. Where included, a surfactant may be present from 0.05%, from 0.1%, up to 10%, up to 5%, up to 4%, up to 3%, up to 2%, or up to 1% by weight of the cleaning composition. Various surfactants and other optional adjuvants are disclosed in U.S. Pat. No. 3,929,678 to Laughlin and Heuring, U.S. Pat. No. 4,259,217 to Murphy, U.S. Pat. No. 5,776,872 to Giret et al.; U.S. Pat. No. 5,883,059 to Furman et al.; U.S. Pat. No. 5,883,062 to Addison et al.; U.S. Pat. No. 5,906,973 to Ouzounis et al.; U.S. Pat. No. 4,565,647 to Llenado, and U.S. Publication No. 2013/0028990. The above patents and applications are each herein incorporated by reference in their entirety.

Examples of nonionic surfactants include, but are not limited to, alcohol ethoxylates, alcohol propoxylates, other alcohol alkoxylates including fatty (e.g., $C_6$, $C_8$, $C_{10}$, or $C_{12}$, or higher) alcohols or other constituents that have been alkoxylated to include both ethoxy and propoxy groups (EO-PO surfactants), alkyl phosphine oxides, alkyl glucosides and alkyl pentosides, alkyl glycerol esters, alkyl ethoxylates, and alkyl and alkyl phenol ethoxylates of all types, poly alkoxylated (e.g. ethoxylated or propoxylated) $C_6$-$C_{12}$ linear or branched alkyl phenols, $C_6$-$C_{22}$ linear or branched aliphatic primary or secondary alcohols, and $C_2$-$C_8$ linear or branched aliphatic glycols. Block or random copolymers of $C_2$-$C_6$ linear or branched alkylene oxides may also be suitable nonionic surfactants. Capped nonionic surfactants in which the terminal hydroxyl group is replaced by halide; $C_1$-$C_8$ linear, branched or cyclic aliphatic ether; $C_1$-$C_8$ linear, branched or cyclic aliphatic ester; phenyl, benzyl or $C_1$-$C_4$ alkyl aryl ether; or phenyl, benzyl or $C_1$-$C_4$ alkyl aryl ester may also be used. Sorbitan esters and ethoxylated sorbitan esters may also be useful nonionic surfactants. Other suitable nonionic surfactants may include mono or polyalkoxylated amides of the formula $R^1CONR^2R^3$ and amines of the formula $R^1NR^2R^3$ wherein $R^1$ is a $C_5$-$C_{31}$ linear or branched alkyl group and $R^2$ and $R^3$ are $C_1$-$C_4$ alkyl, $C_1$-$C_4$ hydroxyalkyl, or alkoxylated with 1-3 moles of linear or branched alkylene oxides. Biosoft 91-6 (Stepan Co.) is an example of an alkyl ethoxylate (or alcohol ethoxylate) having a methylene chain length of $C_9$ to $C_{11}$ with an average of 6 moles of ethoxylation. An example of an alcohol ethoxylate is ECOSURF EH-9, which is more specifically an ethylene oxide-propylene oxide copolymer mono(2-ethylhexyl) ether, available from Sigma-Aldrich.

Alkylpolysaccharide nonionic surfactants are disclosed in U.S. Pat. No. 4,565,647 to Llenado, having a linear or branched alkyl, alkylphenyl, hydroxyalkyl, or hydroxyalkylphenyl group containing from 6 to 30 carbon atoms and a polysaccharide, e.g., a polyglycoside, hydrophilic group containing from 1.3 to 10 saccharide units. Suitable saccharides may include, but are not limited to, glucosides, galactosides, lactosides, and fructosides. Alkylpolyglycosides may have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 10.

Fatty acid saccharide esters and alkoxylated fatty acid saccharide esters may also be suitable for use in the present invention. Examples include, but are not limited to, sucrose esters, such as sucrose cocoate, and sorbitan esters, such as polyoxyethylene(20) sorbitan monooleate and polyoxyethylene(20) sorbitan monolaurate.

Phosphate ester surfactants may also be suitable. These include mono, di, and tri esters of phosphoric acid with $C_4$-$C_{18}$ alkyl, aryl, alkylaryl, alkyl ether, aryl ether and alkylaryl ether alcohols (e.g. disodium octyl phosphate).

Zwitterionic surfactants may be suitable. As zwitterionic surfactants include both a positive and negative functional group, they may also be classified as nonionic surfactants. Many such zwitterionic surfactants contain nitrogen. Examples of such include amine oxides, sarcosinates, taurates and betaines. Examples include $C_8$-$C_{18}$ alkyldimethyl amine oxides (e.g., octyldimethylamine oxide, lauryldimethylamine oxide (also known as lauramine oxide), and cetyldimethylamine oxide), $C_4$-$C_{16}$ dialkylmethylamine oxides (e.g. didecylmethylamine oxide), $C_8$-$C_{18}$ alkyl morpholine oxide (e.g. laurylmorpholine oxide), tetra-alkyl diamine dioxides (e.g. tetramethyl hexanane diamine dioxide, lauryl trimethyl propane diamine dioxide), $C_8$-$C_{18}$ alkyl betaines (e.g. decylbetaine and cetylbetaine), $C_8$-$C_{18}$ acyl sarcosinates (e.g. sodium lauroylsarcosinate), $C_8$-$C_{18}$ acyl $C_1$-$C_6$ alkyl taurates (e.g. sodium cocoylmethyltaurate), $C_8$-$C_{18}$ alkyliminodipropionates (e.g. sodium lauryliminodipropionate), and combinations thereof. Lauryl dimethyl amine oxide (Ammonyx LO) myristyl dimethyl amine oxide (Ammonyx MO), decylamine oxide (Ammonyx DO) are examples of suitable zwitterionic surfactants, available from Stepan Co.

Non-limiting examples of anionic surfactants include alkyl sulfates (e.g., $C_8$-$C_{18}$ linear or branched alkyl sulfates such as sodium lauryl sulfate (SLS), and sodium tetradecylsulfate), alkyl sulfonates (e.g., $C_6$-$C_{18}$ linear or branched alkyl sulfonates such as sodium octane sulfonate and secondary alkane sulfonates, alkyl ethoxysulfates, fatty acids and fatty acid salts (e.g., $C_6$-$C_{16}$ fatty acid soaps such as sodium laurate), and alkyl amino acid derivatives. Other examples may include sulfate derivatives of alkyl ethoxylate propoxylates, alkyl ethoxylate sulfates, alpha olefin sulfonates, $C_6$-$C_{16}$ acyl isethionates (e.g. sodium cocoyl isethionate), $C_6$-$C_{18}$ alkyl, aryl, or alkylaryl ether sulfates, $C_6$-$C_{18}$ alkyl, aryl, or alkylaryl ether methylsulfonates, $C_6$-$C_{18}$ alkyl, aryl, or alkylaryl ether carboxylates, sulfonated alkyldiphenyloxides (e.g. sodium dodecyldiphenyloxide disulfonate), and the like.

More specific examples of nonionic and/or zwitterionic surfactants include lauryl dimethyl amine oxide (Ammonyx LO), also known as lauramine oxide, myristyl dimethyl amine oxide (Ammonyx MO), decylamine oxide (Ammonyx DO), other amine oxides, any betaines, linear alcohol ethoxylates, alcohol propoxylates, alkyl polyglucosides, and combinations thereof.

D. Additional Adjuvants

The cleaning composition may optionally include and/or be used in combination with one or more additional adjuncts. The adjuncts include, but are not limited to, fragrances or perfumes, waxes, dyes and/or colorants, solubilizing materials, stabilizers, thickeners, defoamers, hydrotropes, buffers, builders, lotions and/or mineral oils, enzymes, bleaching agents, cloud point modifiers, and/or preservatives. A variety of builder detergents can be used in and/or used in combination with the cleaning composition. Such builder detergents include, but are not limited to, phosphate-silicate compounds, zeolites, alkali metal, ammonium and substituted ammonium polyacetates, mono-, di-, and tri-alkali salts of nitrilotriacetic acid, carboxylates, aluminosilicate materials, silicates, polycarboxylates, zeolites, carbonates, phosphates, bicarbonates, polyphosphates, amines, alkanolamines, aminopolycarboxylates, polyhydroxysulfonates, starch derivatives, ethylenediamine tetraacetate, and/or metal ion sequestrants (e.g., aminopolyphosphonates such as, but not limited to, ethylenediamine tetramethylene phosphonic acid and diethylene triamine pentamethylenephosphonic acid).

In one embodiment, the builder detergent includes polyacetate and/or polycarboxylate compounds. In one aspect of this embodiment, the polyacetate and/or polycarboxylate compounds include, but are not limited to, sodium, potassium, lithium, ammonium, and substituted ammonium salts of ethylenediamine tetraacetic acid, ethylenediamine tri-acetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid.

In one embodiment, the buffering and pH adjusting agents, when used, include, but are not limited to, organic acids, mineral acids, alkali metal and alkaline earth salts of citrate, silicate, metasilicate, polysilicate, borate, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and/or 2-amino-2methylpropanol.

A buffering agent can be an active detergent in its own right, and/or can be a low molecular weight, organic or inorganic material used for maintaining the desired pH. The buffer can be alkaline, acidic or neutral. Non-limiting examples of buffering agents include nitrogen-containing materials (e.g., lysine; lower alcohol amines like mono-, di-, and tri-ethanolamine; tri(hydroxymethyl) amino methane; 2-amino-2-ethyl-1,3-propanediol; 2-amino-2-methyl-propanol; 2-amino-2-methyl-1,3-propanol; disodium glutamate; methyl diethanolamide; 2-dimethylamino-2-methylpropanol; 1,3-bis(methylamine)-cyclohexane; 1,3-diamino-propanol N,N'-tetra-methyl-1,3-diamino-2-propanol; N,N-bis(2-hydroxyethyl)glycine; tris(hydroxymethyl)methyl glycine; ammonium carbamate; citric acid; acetic acid; ammonia; alkali metal carbonates; and/or alkali metal phosphates). For additional buffers that can be used, see McCutcheon's EMULSIFIERS AND DETERGENTS, North American Edition, 1997, McCutcheon Division, MC Publishing Company which is incorporated herein by reference. In yet another and/or alternative embodiment, solubilizing materials, when used, can include, but are not limited to, hydrotropes (e.g., water soluble salts of low molecular weight organic acids such as the sodium and/or potassium salts of xylene sulfonic acid). In another and/or alternative embodiment, the acids, when used, include, but are not limited to, organic hydroxy acids, citric acids, keto acid, and the like.

In still another and/or alternative embodiment, thickeners, when used, include, but are not limited to, polyacrylic acid, xanthan gum, calcium carbonate, aluminum oxide, alginates, guar gum, methyl, ethyl, clays, and/or propylhydroxycelluloses. In yet another and/or alternative embodiment, defoamers, when used, include, but are not limited to, silicones, aminosilicones, silicone blends, and/or silicone/hydrocarbon blends. In yet a further and/or alternative embodiment, bleaching agents, when used, include, but are not limited to, peracids, perborates, percarbonates, chlorine-generating substances (e.g., chloroisocyanurates hypohalite sources), hydrogen peroxide, and/or sources of hydrogen peroxide. In still a further and/or alternative embodiment, preservatives, when used, include, but are not limited to, mildewstats or bacteriostats, methyl, ethyl and propyl parabens, short chain organic acids (e.g., acetic, lactic and/or glycolic acids), bisguanidine compounds (e.g., Dantagard and/or Glydant) and/or short chain alcohols (e.g., ethanol and/or IPA). In one aspect of this embodiment, the mildewstats or bacteriostats include, but are not limited to, mildewstats (including non-isothiazolone compounds) include Kathon GC, a 5-chloro-2-methyl-4-isothiazolin-3-one, Kathon ICP, a 2-methyl-4-isothiazolin-3-one, and a blend thereof, and Kathon 886, a 5-chloro-2-methyl-4-isothiazolin-3-one, all available from Rohm and Haas Company;

Bronopol, a 2-bromo-2-nitropropane-1,3-diol, from Boots Company Ltd.; Proxel CRL, a propyl-p-hydroxybenzoate, from ICI PLC; Nipasol M, an o-phenyl-phenol, Na+ salt, from Nipa Laboratories Ltd.; Dowicide A, a 1,2-Benzoiso-thiazolin-3-one, from Dow Chemical Co.; and Irgasan DP 200, a 2,4,4'-trichloro-2-hydroxydiphenylether, from Ciba-Geigy A.G.

E. Other Characteristics

As used herein the term "liquid" and "cleaning composition" includes, but is not limited to, solutions, emulsions, suspensions and so forth. Thus, liquid cleaning compositions may comprise and/or contain one or more of the following: disinfectants; antiseptics; sterilants; sporicides; germicides; bactericides; fungicides; virucides; protozoacides; algicides; bacteriostats; fungistats; virustats; sanitizers; antibiotics; pesticides; other antimicrobial agents; diluents; surfactants, such as nonionic, anionic, cationic; waxes; and so forth. Examples of some such components are included in, but not limited to, U.S. Pat. Nos. 6,825,158; 8,648,027; 9,006,165; 9,234,165; 9,988,594; 10,421,929 and U.S. Publication No. 2008/003906, each of which is herein incorporated by reference in its entirety.

Additional non-limiting examples of cleaning compositions and components which may be included in the present embodiments are disclosed in U.S. Pat. No. 5,460,833 to Andrews et al.; U.S. Pat. No. 6,221,823 to Crisanti; U.S. Pat. No. 6,346,279 to Rochon et al.; U.S. Pat. No. 6,551,980 to Wisniewski et al.; U.S. Pat. No. 6,699,825 to Rees et al.; U.S. Pat. No. 6,803,057 to Ramirez et al.; U.S. Pat. No. 6,812,196 to Rees et al.; U.S. Pat. No. 6,936,597 to Urban; U.S. Pat. No. 7,008,600 to Katsigras et al.; U.S. Pat. No. 7,070,737 to Bains et al.; U.S. Pat. No. 7,354,604 to Ramirez et al.; U.S. Pat. No. 7,598,214 to Cusack et al.; U.S. Pat. No. 7,605,096 to Tamarchio et al.; U.S. Pat. No. 7,658,953 to Bobbert; U.S. Pat. No. 7,696,143 to McCue et al.; U.S. Pat. No. 7,915,207 to Chopskie et al.; U.S. Pat. No. 8,569,220 to Gaudrealt; U.S. Pat. No. 8,575,084 to Gaudrealt; U.S. Pat. No. 10,064,409 to Hazenkamp et al.; U.S. Pat. No. 10,076,115 to Salminen et al.; U.S. Pat. No. 10,358,624 to Mitchell et al.; U.S. Publication No. 2007/0190172 to Bobbert; PCT Publication Nos. WO 99/18180 to Raso et al.; WO 99/53006 to Masotti et al.; WO 2004/067194 to Arrigoni et al.; WO 2004/104147 to Rosiello et al.; WO 2017/174959 to Convery; and EPO Publication EP 2843034 to Nedic et al., each of which is herein incorporated by reference in its entirety. Of course, any components or compositions from such must be such so that the resulting wipe can meet requirements for compostability under ASTM D6400, EN13432 or similar standard.

In some embodiments, it may be possible to provide the substrates in dry form, where dosing with a selected disinfection, sanitization, or even another cleaning composition may occur later (e.g., by the user). In another embodiment, the wipes may be dosed with a solid disinfecting, sanitizing or other cleaning composition, where the user may add water to the wipes, at or shortly before the time of use, resulting in the dosed wipes, ready for use. Pre-dosed wipes may be preferred, e.g., as the amount and concentrations of the components in the cleaning composition, and the loading ratio of such composition relative to the absorbent substrate can be more carefully controlled during manufacture, than may occur where the final composition may depend on the user for dilution or water addition.

With regard to pre-moistened substrates, a selected amount of liquid may be added to the container or wipes during manufacture such that the cleaning substrates contain the desired amount of liquid. The substrates are not necessarily loaded to their saturation point, but are typically loaded with the cleaning composition to some ratio less than full saturation. For example, many substrates are capable of holding about 8 to 14 times their weight in liquid. For various reasons, one of such is that loading ratio can affect the ability to achieve compostability under ASTM D6400, EN13432 or similar standard, the substrates may be loaded at a loading ratio less than saturation, e.g., less than 8:1, less than 7:1, less than 6:1, less than 5:1, less than 4.5:1, less than 4:1, such as from 1:1 to 6:1, from 2:1 to 5:1, from 2.5:1 to 4.5:1, or from 3:1 to 4:1.

It is important to understand and account for how the substrate materials affect the chemistry of the cleaning composition being dosed onto the wipes. For example, it can be important to avoid or minimize unwanted chemical interactions that may inadvertently deactivate the active agents within the cleaning composition. It is also important to ensure that the wipe as a whole, once loaded, can meet the requirements for compostability under ASTM D6400, EN13432 or the like. For example, incompatibility between components in the composition versus the substrate can occur, which would be undesirable. The composition that is released from the pre-loaded wipe is referred to as the "squozate". When components of a composition react with or bind to a substrate, the composition that is loaded onto the substrate differs from the "squozate". It is desirable that an effective amount of any given active agent not only be loaded into the wipe, but actually be released in the "squozate" from such wipe, during use.

The size and shape of the wipe can vary with respect to the intended application and/or end use of the same. The cleaning substrate can have a substantially rectangular shape of a size that allows it to readily engage standard cleaning equipment or tools such as, for example, mop heads, duster heads, brush heads, mitten shaped tools for wiping or cleaning, and so forth. In another embodiment, another shape, e.g., circular, oval, or the like) may be provided.

The wipes or other cleaning substrates may be provided pre-moistened with a disinfecting, sanitizing, or other cleaning composition. The wet cleaning substrates can be maintained over time in a sealable container such as, for example, within a bucket or tub with an attachable lid, sealable bags, plastic pouches (e.g., "flex packs"), canisters, jars, and so forth. Desirably the wet, stacked cleaning substrates are maintained in a resealable container. The use of a resealable container is particularly desirable when using aqueous volatile liquid compositions since substantial amounts of water or other liquid can evaporate while using the first sheets thereby leaving the remaining sheets with little or no liquid. Exemplary resealable containers and dispensers include, but are not limited to, those described in U.S. Pat. No. 4,171,047 to Doyle et al., U.S. Pat. No. 4,353,480 to McFadyen, U.S. Pat. No. 4,778,048 to Kaspar et al., U.S. Pat. No. 4,741,944 to Jackson et al., U.S. Pat. No. 5,595,786 to McBride et al.; the entire contents of each of the aforesaid references are incorporated herein by reference.

Typically, the disinfecting, sanitizing, or other cleaning substrates are stacked and placed in the container and the liquid subsequently added thereto, all during mass manufacturing. No matter the packaging and dosing process, once manufactured and packaged, the substrate can subsequently be used to wipe a surface. The moistened cleaning substrates can be used to treat various surfaces. As used herein "treating" surfaces is used in the broad sense and includes, but is not limited to, wiping, polishing, swabbing, cleaning, washing, disinfecting, scrubbing, scouring, sanitizing, and/or applying active agents thereto.

The wipes or other cleaning substrates of the present invention can be provided in a kit form, wherein a plurality of cleaning substrates and a cleaning tool are provided in a single package.

In addition to material composition and construction, wipe or other substrate dimensions can also be used to control dosing as well as provide ergonomic appeal. In one embodiment, substrate dimensions are from about 5½ inches to about 11 inches in length, and from about 5½ inches to about 11 inches in width to comfortably fit in a hand. The substrate can have dimensions such that the length and width differ by no more than about 2 inches. Larger substrates may be provided that can be used and then folded, either once or twice, so as to contain dirt within the inside of the fold and then the wipe can be re-used. Such larger substrates may have a length from about 5½ inches to about 13 inches and a width from about 10 inches to about 13 inches. Such substrates can be folded once or twice and still fit comfortably in the hand. As described above, the substrates may be sufficiently thin to have a basis weight of no more than 200 gsm, no more than 150 gsm, no more than 100 gsm, such as from 5 to 80 gsm, or from 10 to 60 gsm. Such thin characteristics may be important to the ability to meet the compostability or biodegradability standards under ASTM D6400, EN13432, or other applicable standard. For example, significantly thicker substrates may not meet the biodegradation and/or disintegration standards applicable under ASTM D6400, EN13432, or the like.

Exemplary multi-layer substrates can be tested for their ability to effectively deliver an antimicrobial quaternary ammonium compound ("quat") or other active agent to a surface during simulated cleaning. By way of example, the substrates of the present invention may be loaded with cleaning compositions including from 0.1% to 3%, such as 0.1% to 2% by weight of the quaternary ammonium compound. In an embodiment, the wipes may release at least 40%, at least 50%, at least 55%, at least 60%, or at least 65% of the quaternary ammonium compound (i.e., quaternary ammonium compound in the squozate (i.e. the cleaning composition released from the substrate) as compared to the Table 1 below, and are laid out in ASTM D6400, herein incorporated by reference in its entirety.

TABLE 1

| Require-ment | Qualification Determined Through: | Methodology |
|---|---|---|
| (1) Heavy Metals | Chemical characteristics analysis: Heavy metals concentration must be <50% of those allowed in sludges and composts in the U.S. | ASTM D6400 ASTM D6868 for a material including a polymer |
| (2) Biode-gradation | Carbon dioxide conversion determination: 90% of organic carbon converted to carbon dioxide within 180 days, for whole item or each organic constituent present at >1% dry mass. | ASTM D6400 ASTM D5338 (aerobic conditions) ASTM D5511 and ASTM D5526 (anaerobic conditions) |
| (3) Disinte-gration | Quantitative disintegration test: 90% disintegration required within 12 weeks using ISO 16929 or ISO 20200 | ASTM D6400 |
| (4) Plant Toxicity | Germination and biomass testing: Germination rate and plant biomass of the sample compost must be ≥90% of control compost for 2 plant species following OECD guideline 208 with modifications from Annex E of EN13432 | ASTM D6400 |

*The year of original adoption for D6400, D6868, D5338, D5511, and D5526 is 2012, 2017, 2015, 2018, and 2012, respectively.

An exemplary formulation is shown below in Table 2A, and was evaluated for weight percent solids, for each given component.

TABLE 2A

| Component | Wt % as is (of Composition) | % Total Solids | Dry weight % | Dry Wt % of final product | Known Biodegradability |
|---|---|---|---|---|---|
| Water | 96.43% | | | | |
| Organic Acid | 0.01% | 100% | 0.01% | 0.02% | Yes |
| Builder | 0.01% | 100% | 0.01% | 0.02% | |
| Glycol ether solvent | 1.83% | 0% | 0% | 0% | |
| $C_{12}$-$C_{14}$ fatty alcohol alkoxylate | 0.44% | 80% | 0.35% | 1.37% | |
| First and second quaternary ammonium compounds | 0.73% | 50% | 0.37% | 1.43% | |
| Fragrance | 0.10% | 7% | 0.007% | 0.03% | |
| $C_1$-$C_4$ alcohol solvent | 0.45% | 0% | 0% | 0% | |
| Substrate | | 100% | | 97.13% | | cleaning composition before loading). The wipes may exhibit at least a 3-log reduction in a target microbe, such as *Staphylococcus aureus*, within a given contact time time frame (e.g., such as 5 minutes, 4 minutes, 3 minutes, 1 minute, 30 seconds, etc.).

IV. Examples

In order to meet the compostability requirements under ASTM D6400, four basic requirements must be met: (1) lack of heavy metals; (2) pass biodegradation test under controlled composting conditions; (3) disintegration; and (4) lack of plant toxicity. These requirements are summarized in The weight percent solids for each component shown in Table 2A were determined by oven drying the components at 105° C. for 4 days. The nonionic $C_{12}$-$C_{14}$ fatty alcohol alkoxylate surfactant and the quaternary ammonium compounds are the only ingredients present at >1% dry weight of the final loaded wipe (at a loading ratio of 4:1). Because the quaternary ammonium component is actually a mixture of two quats, they can be treated separately, and each on its own is present at <1% dry weight of the final loaded wipe. As such, only the $C_{12}$-$C_{14}$ fatty alcohol alkoxylate surfactant must be tested separately for compliance with the biodegradation testing portion of the ASTM D6400 standard.

Table 2B shows another formulation, evaluated under the same standards as the evaluation of Table 2A.

TABLE 2B

| Component | Wt % as is (of Composition) | % Total Solids | Dry weight % | Dry Wt % of final product | Known Biodegradability |
|---|---|---|---|---|---|
| Water | 97.34% | | | | |
| nonionic surfactant | 0.35% | 30% | 0.11% | 0.34% | |
| Glycol ether solvent | 1.00% | 0% | 0% | 0% | |
| $C_1$-$C_4$ alcohol solvent | 0.45% | 0% | 0% | 0% | |
| First and second quaternary ammonium compounds | 0.73% | 50% | 0.37% | 1.18% | |
| Fragrance | 0.12% | 5% | 0.006% | 0.02% | |
| Substrate | | 100% | | 98.46% | |

The weight percent solids for each component shown in Table 2B were determined by a similar method as those in Table 2A. The quaternary ammonium is the only ingredient present at >1% dry weight of the final loaded wipe (at a loading ratio of 3.25:1). Because the quaternary ammonium component is actually a mixture of two quats, they can be treated separately, and each on its own is present at <1% dry weight of the final loaded wipe. As such, none of the components in the Table 2B formulation must be tested separately for compliance with the biodegradation testing portion of the ASTM D6400 standard.

Table 2C shows another formulation, evaluated under the same standards as the evaluation of Table 2A.

TABLE 2C

| Component | Wt % as is (of Composition) | % Total Solids | Dry weight % | Dry Wt % of final product | Known Biodegradability |
|---|---|---|---|---|---|
| Water | 98.15% | | | | |
| Defoamer | 0.02% | 100% | 0.02% | 0.06% | |
| nonionic surfactant | 0.28% | 62% | 0.17% | 0.67% | |
| $C_1$-$C_4$ alcohol solvent | 0.45% | 0% | 0% | 0% | |
| Glycerin | 0.11% | 100% | 0.11% | 0.43% | |
| preservative | 0.08% | 10% | 0.01% | 0.03% | |
| antifungal | 0.10% | 6% | 0.01% | 0.02% | |
| Builder | 0.32% | 47% | 0.15% | 0.58% | |
| Buffer | 0.15% | 100% | 0.15% | 0.58% | |
| Fragrance | 0.15% | 5% | 0.008% | 0.03% | |
| Organic Acid (50%) | 0.10% | 50% | 0.05% | 0.19% | Yes |
| pH Adjusting Agent (50%) | 0.10% | 50% | 0.05% | 0.19% | Yes |
| Substrate | | 100% | | 97.22% | |

The weight percent solids for each component shown in Table 2C were determined by a similar method as those in Table 2A. Because none of the components are present at >1% dry weight of the final loaded wipe (at the loading ratio of 4:1), none of the components in the Table 2C formulation must be tested separately for compliance with the biodegradation testing portion of the ASTM D6400 standard.

Table 2D shows another formulation, evaluated under the same standards as the evaluation of Table 2A.

TABLE 2D

| Component | Wt % as is (of Composition) | % Total Solids | Dry weight % | Dry Wt % of final product | Known Biodegradability |
|---|---|---|---|---|---|
| Water | 97.23% | | | | |
| Nonionic surfactant | 2.01% | 50% | 1.01% | 6.66% | |
| $C_1$-$C_4$ alcohol solvent | 0.34% | 0% | 0% | 0% | |
| Preservative | 0.08% | 10% | 0.01% | 0.05% | |
| Antifungal | 0.10% | 5% | 0.01% | 0.03% | |
| Builder | 0.24% | 47% | 0.11% | 0.74% | |
| Buffer | 0.11% | 100% | 0.11% | 0.75% | |
| Fragrance | 0.09% | 5% | 0.005% | 0.03% | |
| Organic Acid (50%) | 0.05% | 50% | 0.03% | 0.18% | |
| Sodium gluconate | 0.15% | 100% | 0.15% | 0.99% | |
| Substrate | | 100% | | 90.57% | |

The weight percent solids for each component shown in Table 2D were determined by a similar method as those in Table 2A. The nonionic surfactant is the only ingredient present at >1% dry weight of the final loaded wipe (at a loading ratio of 7.3:1). As such, the nonionic surfactant in the Table 2D formulation would need to be tested separately for compliance with the biodegradation testing portion of the ASTM D6400 standard.

Table 2E shows a comparative formulation, based on citric-acid as an antimicrobial agent, evaluated under the same standards as the evaluation of Table 2A.

Figure 1B:
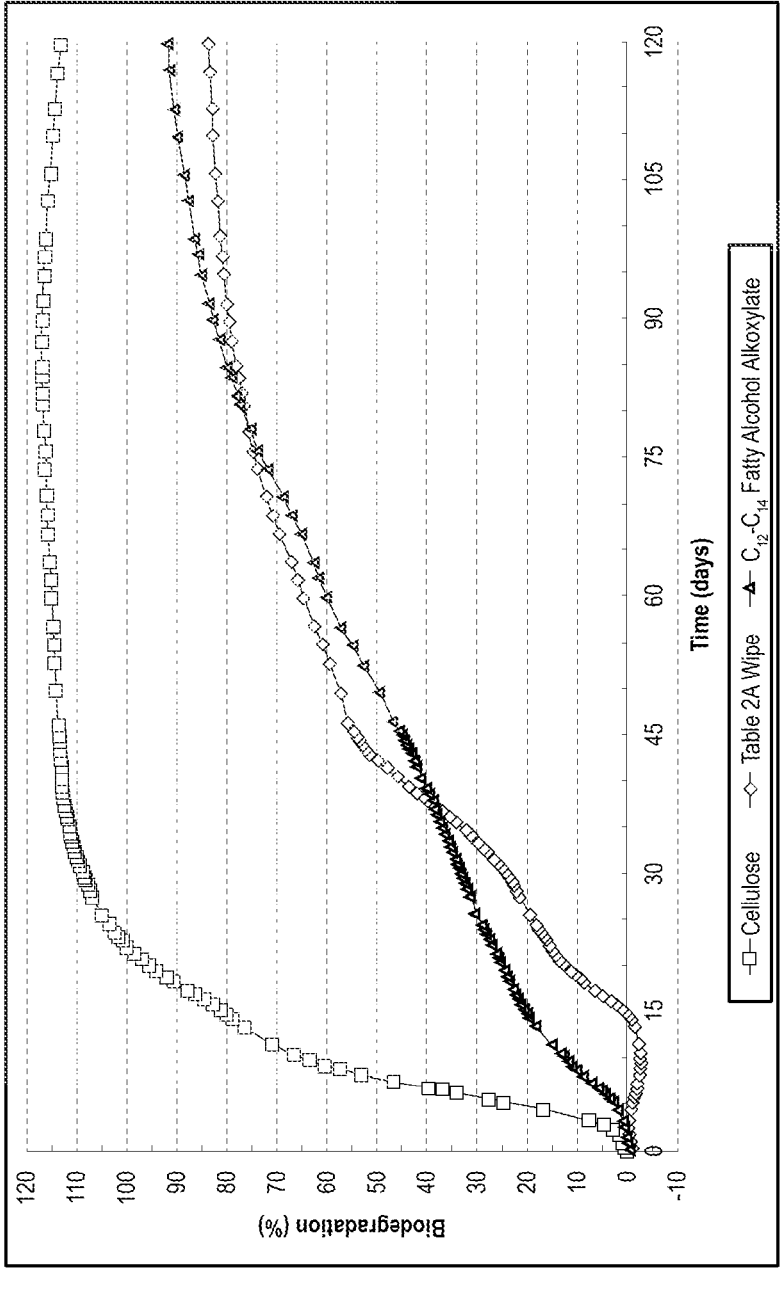
FIG. 1B charts the average biodegradation over time, using ASTM D5338, for Dehypon LS54 surfactant alone (as in FIG. 1A), as well as average biodegradation over time for a viscose/lyocell substrate wipe dosed with the composition of Table 2A, including Dehypon LS54, against a cellulose positive control.

As the formulation of Table 2A includes greater than 1% dry weight of the $C_{12}$-$C_{14}$ fatty alcohol alkoxylate surfactant, in the loaded wipe, as a whole, biodegradation testing was conducted on this surfactant. The results are shown in FIGS. 1A-1B, where the 3 tested replicates (FIG. 1A) showed an average biodegradation (FIG. 1B) of 92.4% within 120 days, which is sufficient to meet the biodegradation portion of the ASTM D6400 standard. The biodegradation testing for the wipe as a whole (FIG. 1B) had reached 84% within 120 days, and is likely to reach at least 90% biodegradation within 180 days. The cellulose control

TABLE 2E

| Component | Wt % as is (of Composition) | % Total Solids | Dry weight % | Dry Wt % of final product | Known Biodegradability |
|---|---|---|---|---|---|
| Water | 95.23% | | | | |
| Citric Acid (50%) | 1.33% | 50% | 0.67% | 2.56% | |
| secondary alkyl (e.g., $C_{14}$-$C_{17}$) sulfonate | 0.89% | 29% | 0.26% | 0.99% | |
| First glycol ether solvent | 1.05% | 0% | 0% | 0% | |
| Second glycol ether solvent | 0.80% | 0% | 0% | 0% | |
| Alcohol Solvent | 0.30% | 0% | 0% | 0% | |
| Fragrance | 0.10% | 5% | 0.005% | 0.02% | |
| PolyDADMAC | 0.26% | 21% | 0.05% | 0.21% | |
| Thickener | 0.02% | 26% | 0.01% | 0.02% | |
| Defoamer | 0.01% | 100% | 0.01% | 0.04% | |
| Substrate | | 100% | | 96.16% | |

Figure 2:
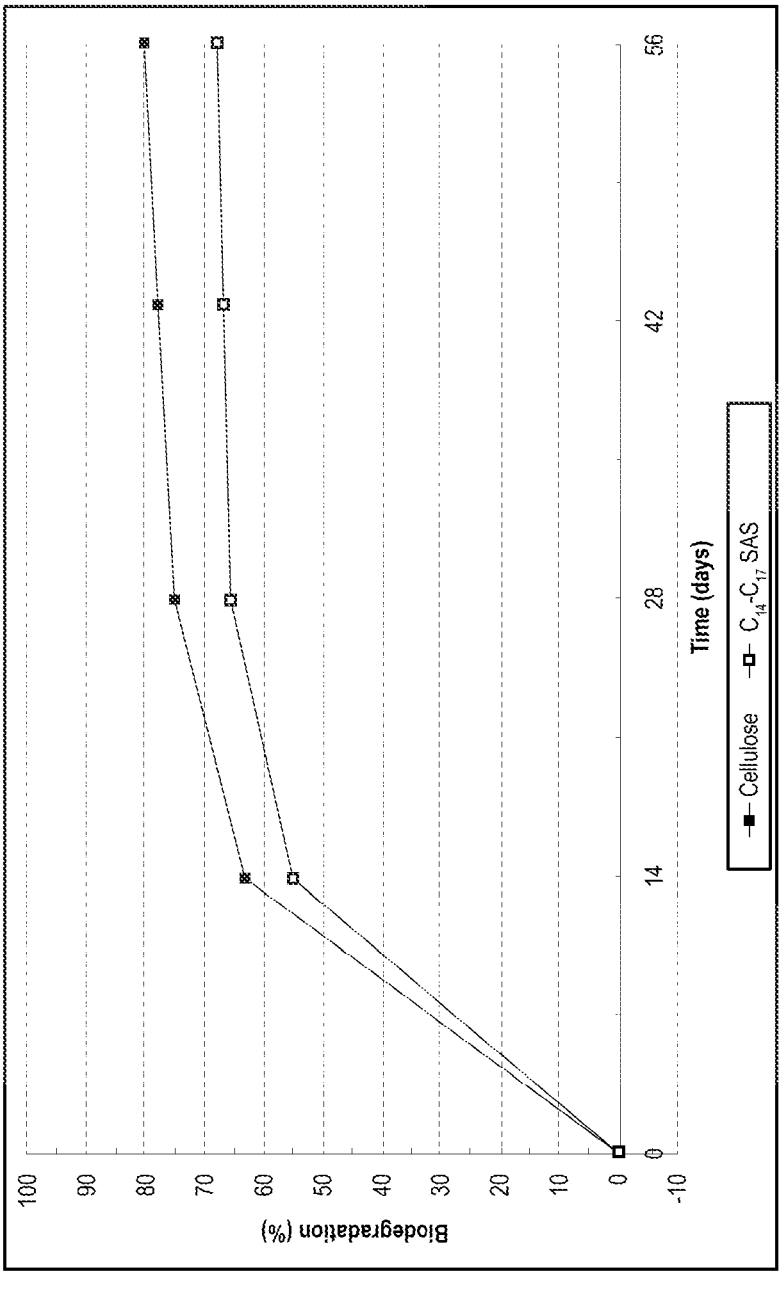
FIG. 2 charts the average biodegradation over time, using ASTM D5271, for a positive cellulose control, against SAS 30, which is an anionic surfactant that is a secondary alkyl (e.g., $C_{14}$-$C_{17}$) sulfonate.

The weight percent solids for each component shown in Table 2E were determined by a similar method as those in Table 2A. The citric acid is the only ingredient present at >1% dry weight of the final loaded wipe (at a loading ratio of 4:1), although the secondary alkyl sulfonate surfactant is essentially on the line, of 1% dry weight. Results for biodegradation of the secondary alkyl sulfonate (under ASTM D6400) are shown in FIG. 2. As shown in FIG. 2, biodegradation of the secondary alkyl sulfonate plateaus after 40-50 days, such that it is unlikely to reach 90% or higher, within 180 days, as required under D6400.

Wipes loaded with the compositions (loading ratio of 4:1) shown in Tables 2A and 2B were tested for antimicrobial efficacy against *Staphylococcus aureus* at a 30 second contact time. The wipes included a viscose/lyocell blended substrate. For each loaded wipe embodiment, a 10 carrier test was conducted, and the results averaged. The results are shown in Table 3.

TABLE 3

| Sample | Contact Time | Log Reduction |
|---|---|---|
| Viscose/Lyocell blended substrate loaded with Table 2A formulation at 4X | 30 sec. | 5.06 |
| Viscose/Lyocell blended substrate loaded with Table 2B formulation at 4X | 30 sec. | 5.75 |

It is apparent from the results of Table 3, that the pre-loaded wipes are capable of providing a significant log reduction in a target microbe (e.g., at least a 3-log, 4-log, or 5-log reduction) within a very short contact time (e.g., as little as 30 seconds). These examples also are capable of meeting the compostability requirements under ASTM D6400, with respect to lack of heavy metals, biodegradation under controlled composting conditions (e.g., 90% or higher biodegradation within 180 days for the preloaded wipe as a whole), disintegration, and lack of plant toxicity.

exhibiting greater than 100% measured biodegradation as shown in FIG. 1B is explained by the priming effect, as will be appreciated by those of skill in the art, familiar with such biodegradation tests. As noted above, FIG. 2 shows biodegradation results, under ASTM D5271, for the secondary alkyl sulfonate surfactant of the formulation of Table 2E, which does not reach 90% biodegradation within 180 days, but plateaus after 40-50 days. ASTM D5271 was developed for measuring biodegradation of activated sludge-wastewater treatment and is an approved substitute method for ASTM D6400. Because biodegradation has plateaued so early, the test is unlikely to reach 90% biodegradation within 180 days.

The viscose/lyocell fibers employed in these examples are certified as biodegradable, having already been tested for biodegradability, heavy metals, and plant toxicity (requirements (1), (2), and (4) of D6400 shown in Table 1). Non-limiting exemplary suppliers of such materials include Lenzing AG, in Lenzing, Austria and Birla Cellulose, in Mumbai, India.

Disintegration testing according to requirement (3) was carried out on 100% viscose and viscose/lyocell blended substrates, under both industrial and home composting conditions. Tested samples under industrial composting conditions had a basis weight of 110 gsm to 115 gsm, and thicknesses of 1.16 mm to 1.21 mm. Testing was conducted according to ISO 16929 (2019). At start up, the test materials were cut into 10 cm×10 cm samples, and were added at a 1% concentration to biowaste for evaluation of their disintegration characteristics during composting. The test was performed in duplicate, and ran for 12 weeks. At the end of the composting test, the composts were sieved and disintegration was evaluated. After 6 weeks of composting, all of the test samples seemed to have disappeared completely. This was confirmed with the turnings at the end of the 12 week test. Disintegration is defined as a size reduction to <2 mm. According to EN 13432 *Requirements for packaging recov-* erable through composting and biodegradation—Test scheme and evaluation criteria for the final acceptance of packaging (2000), the American standard ASTM D6400 Standard Specification for Labeling of Plastics Designed to be Aerobically Composted in Municipal or Industrial Facilities (2019) and the international standard ISO 17088 Specifications for compostable plastics (2012), less than 10% of the material may remain present in the >2 mm fraction after 12 weeks of composting. 100% disintegration was achieved.

Disintegration testing under lower temperature "home" composting conditions (e.g., 28° C.) was also performed, achieving similar 100% disintegration results within the 12 week period.

Additional antimicrobial efficacy testing was conducted using 2 different citric acid-based formulations, e.g., similar to the formulations shown in Table 2E, loaded onto compostable substrates. As shown below in Table 4 the citric acid-based compositions require a significantly longer contact time (e.g., 5 to 8 minutes) to achieve comparable log reductions (e.g., 5+) against Staphylococcus aureus.

TABLE 4

| Sample | Contact Time | Log Reduction |
|---|---|---|
| 1.33% citric acid (similar to Table 2E) | 5 min. | 5.8 |
| 1.33% citric acid (similar to Table 2E) | 8 min. | 5.9 |
| 0.6% citric acid (similar to Table 2E) | 5 min. | 6.2 |

By way of comparison, 60 wipes (10 each of 6 wipes) were tested for antimicrobial efficacy using a quat-based formula similar to that of Table 2A (but including 0.318% total of the two quaternary ammonium compounds), dosed at a loading ratio of 4:1 on 100% lyocell substrates, with results as shown below in Table 5.

TABLE 5

| Sample | Contact Time | Log Reduction |
|---|---|---|
| Wipe 5 | 3:30 min. | 6.57 |
| Wipe 6 | 3:30 min. | 6.57 |
| Wipe 7 | 3:30 min. | 6.54 |
| Wipe 8 | 3:30 min. | 6.57 |
| Wipe 9 | 3:30 min. | 6.57 |
| Wipe 10 | 3:30 min. | 6.54 |

Figure 3:
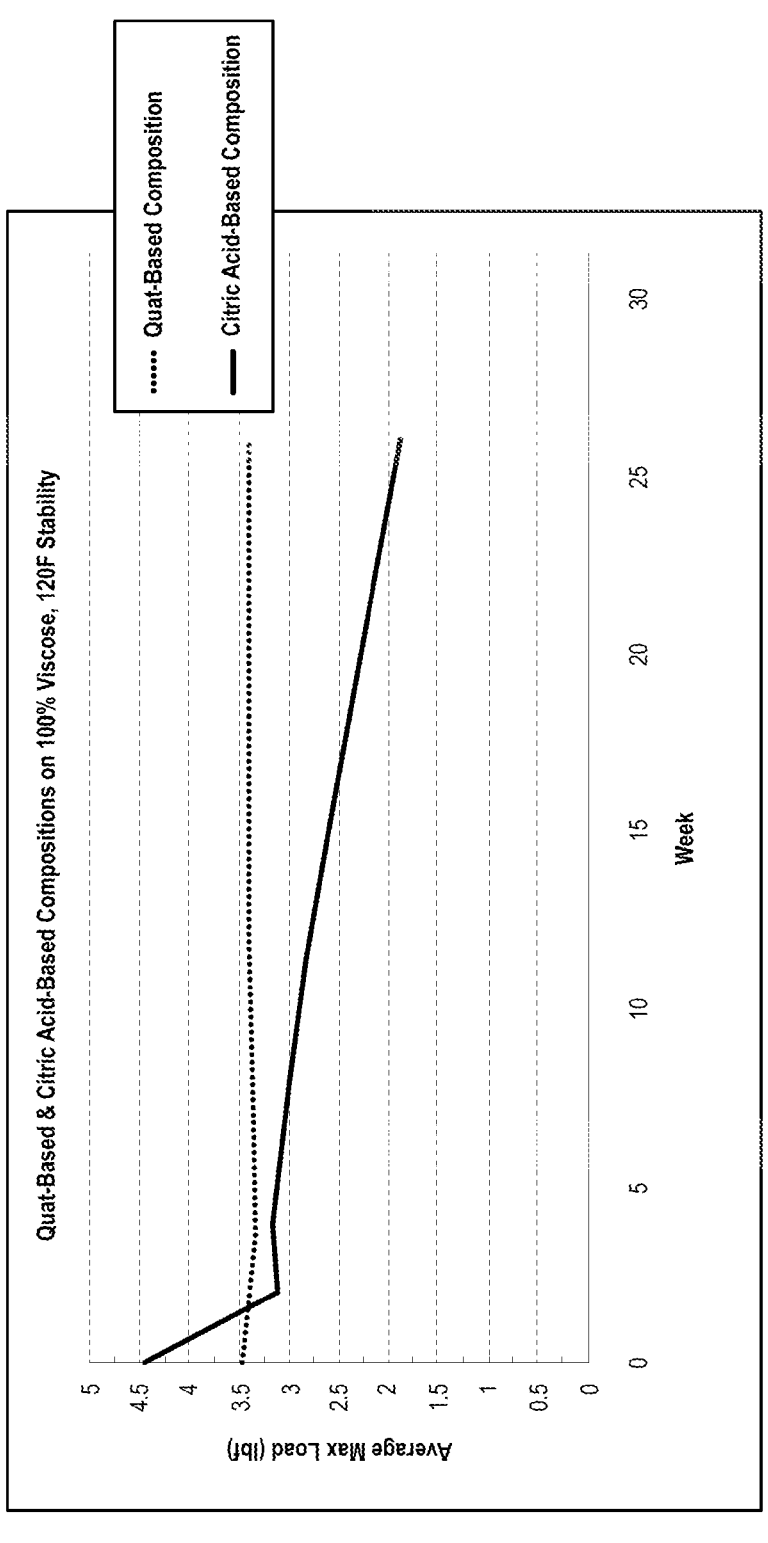
FIG. 3 charts the tensile strength for exemplary pre-loaded wipes over time, for a wipe including a viscose substrate loaded with a citric acid-based composition, as compared to a similar wipe loaded with a quat-based composition.
Figure 4:
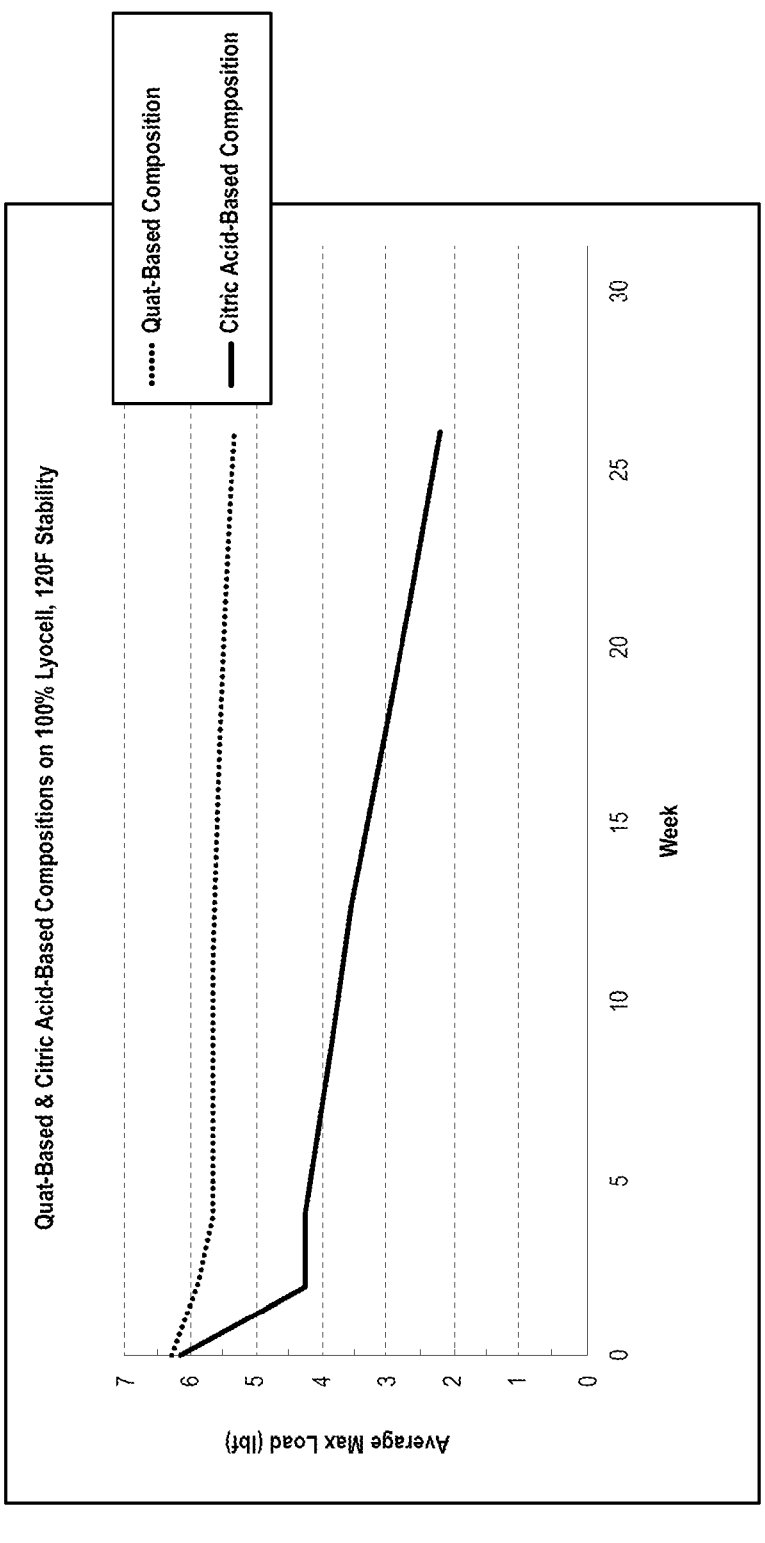
FIG. 4 charts the tensile strength for exemplary pre-loaded wipes over time, for a wipe including a lyocell substrate loaded with a citric acid-based composition, as compared to a similar wipe loaded with a quat-based composition.

FIG. 3 charts tensile strength for both an exemplary quat-based formulation (e.g., the formula of Table 2A) on viscose (e.g., loaded at a 4:1 ratio), as compared to tensile strength for a citric acid-based formulation (e.g., the formulation of Table 2E), also on viscose. As is apparent, when stored at 120° F. (49° C.), the tensile strength in the cross-direction drops relatively quickly when the viscose is dosed with the citric acid-based formulation. Tensile strength values below 3 lb$_f$ are problematic, as they interfere with the ability to reliably dispense the wipes from a typical dispenser, and such weakened wipes are more likely to tear during use, which is frustrating to the user. pH of the composition used to dose the wipes is thus important, to ensure sufficient strength for the contemplated substrates. By way of example, the Table 2A formulation has a pH of 6-8, while that of Table 2E is only 2-3. FIG. 4 illustrates similar test results for these same compositions (Table 2A vs. Table 2E), on a 100% lyocell substrate. The 120° C. (49° C.) temperature of the tests is helpful in simulating what occurs during storage, in an accelerated time frame.

Without departing from the spirit and scope of this invention, one of ordinary skill can make various modifications to the invention to adapt it to various usages and conditions. As such, these changes and modifications are properly, equitably, and intended to be, within the full range of equivalence of the following claims.

The invention claimed is:

1. A sanitizing or disinfecting wipe consisting of:
(i) a nonwoven substrate comprising fibers derived from a renewable plant-based material, wherein the nonwoven substrate comprises lyocell and is void of viscose; and
(ii) a sanitizing or disinfecting composition loaded onto said nonwoven substrate, wherein the sanitizing or disinfecting composition consists of:
(a) at least one quaternary ammonium compound as an antimicrobial agent, wherein the composition does not include carboxylic acid antimicrobial agents, biguanides, peroxides, hypohalites, or other antimicrobial agents;
(b) a surfactant; and
(c) water;
(d) optionally, one or more of fragrances or perfumes, waxes, dyes and/or colorants, solubilizing materials, stabilizers, thickeners, defoamers, hydrotropes, buffers, builders, lotions and/or mineral oils, enzymes, cloud point modifiers, and/or preservatives;
wherein the composition has a pH of at least 5;
wherein the composition provides at least a 3-log reduction against a target microbe within 4 minutes or less;
wherein the sanitizing or disinfecting wipe is compostable as a whole and each component of the composition is present at less than 1% dry weight of the wipe as a whole or components that exceed 1% dry weight of the wipe as a whole all pass a biodegradation test where 90% or more of the component biodegrades within 180 days when tested alone.

2. The wipe of claim 1, wherein the lyocell comprises up to 95% by weight of fibers of the nonwoven substrate.

3. The wipe of claim 1, wherein the nonwoven substrate consists of a blend of lyocell and pulp fibers.

4. The wipe of claim 1, wherein the nonwoven substrate fibers comprise from about 50% to about 95% by weight of lyocell.

5. The wipe of claim 1, wherein the nonwoven substrate is substantially void of polyolefins, polyesters and other synthetic fibers.

6. The wipe of claim 1, wherein the nonwoven substrate is substantially void of thermoplastic fibers.

7. The wipe of claim 1, wherein the at least one quaternary ammonium compound is present as two or more quaternary ammonium compounds, the quaternary ammonium compounds collectively being present in an amount of greater than 1% by dry weight of the wipe as a whole, each of the quaternary ammonium compounds individually being present in an amount of less than 1% by dry weight of the wipe as a whole.

8. The wipe of claim 1, wherein the sanitizing or disinfecting composition comprises at least 90% by weight water.

9. The wipe of claim 1, wherein the sanitizing or disinfecting composition comprises at least 95% by weight water.

10. The wipe of claim 1, wherein the sanitizing or disinfecting composition is loaded onto the nonwoven substrate at a loading ratio of from 2:1 to 8:1 by weight.

11. The wipe of claim 1, wherein the sanitizing or disinfecting composition is loaded onto the nonwoven substrate at a loading ratio of from 2:1 to 6:1 by weight.

12. The wipe of claim 1, wherein the surfactant is present in an amount of greater than 1% by dry weight of the wipe as a whole, and when tested alone, at least 90% of the surfactant biodegrades within 180 days.

13. The wipe of claim 1, wherein the sanitizing or disinfecting composition has a pH from about 6 to about 8.

14. The wipe of claim 1, wherein the composition provides at least a 3-log reduction against a target microbe within 3 minutes or less.

15. The wipe of claim 1, wherein the composition provides at least a 3-log reduction against a target microbe within 1 minute or less.

16. The wipe of claim 1, wherein the surfactant comprises a fatty alcohol alkoxylate, the fatty alcohol alkoxylate surfactant being present in an amount of greater than 1% by dry weight of the wipe as a whole, and when tested alone, at least 90% of the fatty alcohol alkoxylate surfactant biodegrades under within 180 days.

17. The wipe of claim 1, wherein the wipe meets requirements for compostability under at least one of ASTM D6400 or EN13432.

\* \* \* \* \*